(12) United States Patent
Aparicio et al.

(10) Patent No.: US 8,110,393 B2
(45) Date of Patent: Feb. 7, 2012

(54) METHOD AND APPARATUS FOR SEPARATING AND HARVESTING CELLS FROM A WHOLE BLOOD SAMPLE

(75) Inventors: Carlos Aparicio, Miami, FL (US); Enrique Rabellino, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 1304 days.

(21) Appl. No.: 11/690,340

(22) Filed: Mar. 23, 2007

(65) Prior Publication Data

US 2008/0233553 A1   Sep. 25, 2008

(51) Int. Cl.
| | |
|---|---|
| C12M 1/34 | (2006.01) |
| C12M 3/00 | (2006.01) |
| G01N 33/48 | (2006.01) |
| G01N 1/00 | (2006.01) |
| G01N 21/00 | (2006.01) |
| G01N 31/00 | (2006.01) |
| G01N 33/00 | (2006.01) |

(52) U.S. Cl. ............... 435/287.1; 435/288.7; 356/39; 356/36; 422/67

(58) Field of Classification Search ............... 435/287.1, 435/288.7; 356/36, 39; 422/67
See application file for complete search history.

(56) References Cited

U.S. PATENT DOCUMENTS

| | | | | |
|---|---|---|---|---|
| 5,962,237 | A * | 10/1999 | Ts'o et al. | 435/7.23 |
| 7,450,224 | B2 | 11/2008 | Maroney et al. | |
| 2004/0229368 | A1 | 11/2004 | Rubio et al. | |
| 2004/0247487 | A1 * | 12/2004 | Commercon et al. | 422/99 |
| 2006/0077376 | A1 * | 4/2006 | Maroney et al. | 356/39 |

OTHER PUBLICATIONS

GE Healthcare: Instructions 28-4039-56 AC, First published Oct. 2005, 16 pages.*
Merriam Webster Online "predetermine" www.m-w.com 1 page, accessed Jun. 1, 2011.*
E.M. Areman, et al "Automated Isolation of Mononuclear Cells Using the Fenwal CS3000 Blood Cell Separator", Bone Marrow Purging and Processing, pp. 379-385 (1990).
M.H. Goldrosen, et al "Isolation of Human Peripheral Blood Lymphocytes: Modification of a Double Discontinuous Density Gradient of Ficoll-Hypaque", J Immuno Methods, 14, pp. 15-17 (1977).
A. Ferrante, et al "Separation of Mononuclear and Polymorphonuclear Leucocytes from Human Blood by the One-Step Hypaque-Ficoll Method is Dependent on Blood Column Height", J Immuno Methods, 48, pp. 81-85 (1982).
T.B. Casale, et al "A Rapid Method for Isolation of Human Mononuclear Cells Free of Significant Platelet Contamination", J Immuno Methods, 55, pp. 347-353 (1982).
A. Islam, "A New, Fast and Convenient Method for Layering Blood or Bone Marrow Over Density Gradient Medium", J Clin Pathol, 48, pp. 686-688 (1995).
Tissue Culture Facility (online). "General Protocol for the Immortalization of Human B-Lymphocytes Using EBV", Feb. 7, 2007 at <<URL: http://www.unclineberger.org/tcf/protocols_GPI.asp>>, 3 pages.
Glick, et al. "The use of Ficoll-Hypaque double density gradients in the separation of avian granulocytes from other cell types for the purpose of cell flow cytometric analysis", Dev Comp Immunol, Summer 1985, vol. 9, No. 3, pp. 477-484 (Abstract only).
Amersham Biosciences (online). Ficoll-Paque Plus. 2001 at <<URL: http://fachschaft.biochemtech.uni-halle.de/downloads/chromatography/ficoll.pdf>>, 20 pages.
Beckman (online). Coulter PrepPlus Series Workstations. Feb. 17, 2007 at <<URL: http://web.archive.org/web/20070217120603/http://www.beckman.com/products/instrument/flow cytometry/prepplus.asp>>, 2 pages.
Spreckley, K., et al "Automated Blood Fractionation for Biobanking: Benefits and Future Trends", Am Biotech Lab, vol. 27, No. 1, Jan. 2009, pp. 6-9.

* cited by examiner

*Primary Examiner* — Jon P Weber
*Assistant Examiner* — Thane Underdahl
(74) *Attorney, Agent, or Firm* — K&L Gates LLP; Louis C. Cullman; Dean G. Stathakis

(57) ABSTRACT

The present specification discloses an automated method and apparatus useful for separating and harvesting cells of interest, e.g., mononuclear cells, in a whole blood sample. The method of the invention uses the aspirating/dispensing probe of an automated sample preparation instrument to underlay a density gradient medium beneath a whole blood sample in a centrifugation tube, and the same probe is used to harvest cells of interest from a cell layer formed in the tube as a result of a centrifugation step. In harvesting cells, the probe is advanced inside the tube by a fixed, predetermined distance at which the probe tip (i.e., its aspiration port) is known to be located at, or within a predetermined distance below, the bottom of the cell layer. A predetermined volume of liquid is then aspirated through the probe tip, whereby most cells of interest (and more than 90% of those cells that can be harvested by a flawless manual method) are removed from the cell layer and collected for analysis. Preferably, the probe is caused to move laterally with respect to the tube during the aspiration of the cell layer, whereby cells offset from the center of the container are readily harvested.

7 Claims, 8 Drawing Sheets

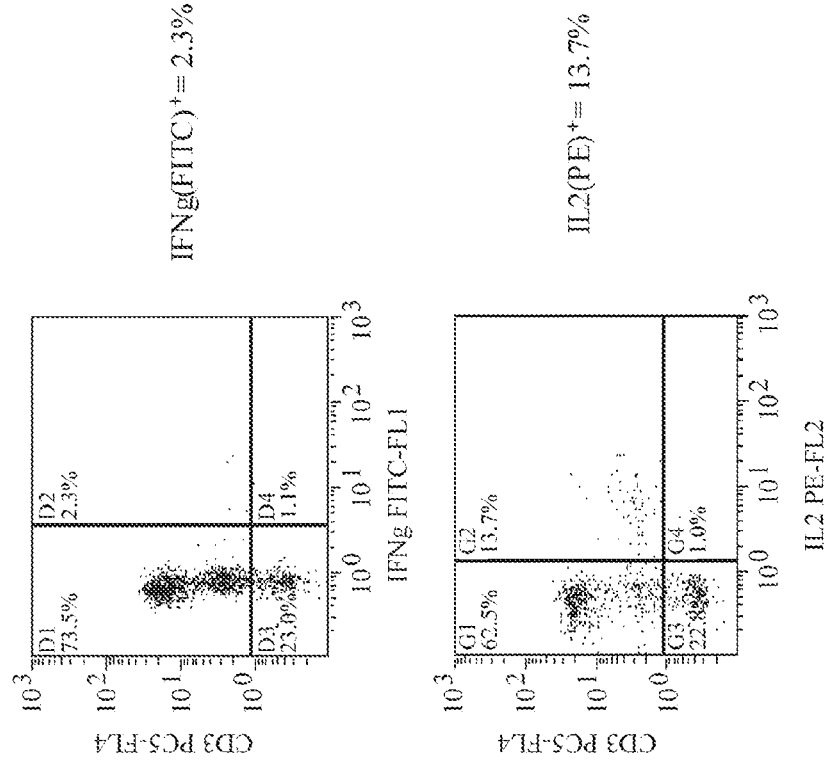
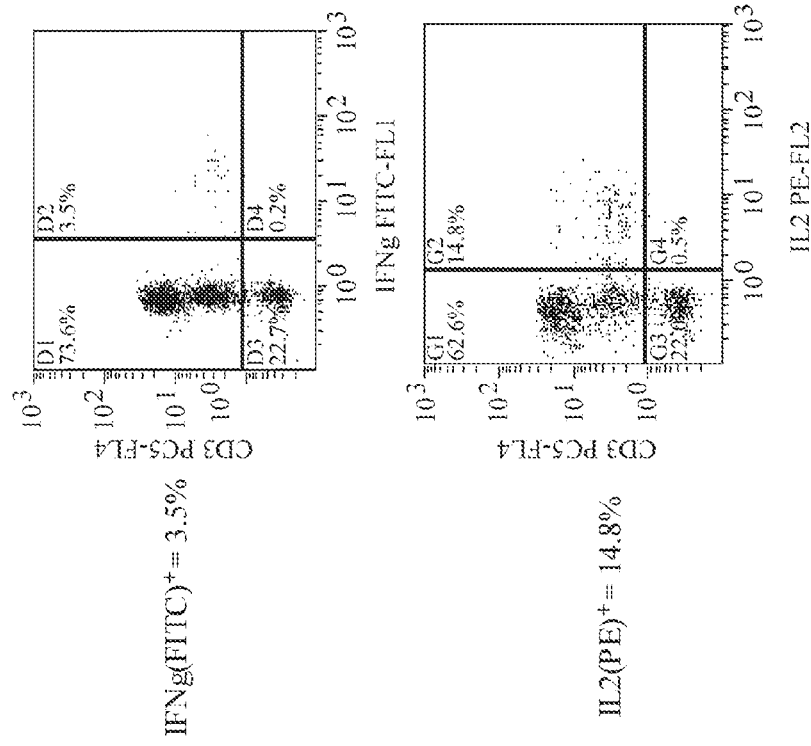

METHOD AND APPARATUS FOR SEPARATING AND HARVESTING CELLS FROM A WHOLE BLOOD SAMPLE

BACKGROUND OF THE INVENTION

1. Field of the Invention

The present invention relates to improvements in methods and apparatus for selectively extracting cells of interest from a whole blood sample. More particularly, it relates to a readily automatable method for separating and harvesting blood cells on the basis of their respective densities.

2. The Prior Art

A detailed characterization of different types of cells, e.g., lymphocytes, monocytes, eosinophils, etc., found in a whole blood sample can provide a phenotypic and functional fingerprint of a patient's immune system at different and various levels of activation. This information is vital to various investigative strategies, e.g., in the pharmaceutical industry, to determine a new drug's efficacy and toxicity. For this purpose, pharmaceutical companies conduct large clinical trials that include multiple sample collection and test sites throughout the world where cells of interest are separated from other cells and harvested for investigation.

To date, the process for preparing blood samples for buoyant density cell separation has been tedious and labor-intensive, as has been the cell-harvesting process itself. The large number of samples and differences in test site practices creates, in general, a difficult challenge for data interpretation and generation of technical conclusions.

Heretofore, it has been common to manually prepare blood samples for mononuclear cell separation by first carefully layering the blood sample atop the surface of a suitable density gradient medium disposed within a centrifugation tube. During this layering process, should any turbulence be created at the sample/density gradient interface, an undetermined number of blood cells will become "lost" within the density gradient material. After layering the blood sample atop the density gradient material, the tube and its contents are subjected to a relatively low speed (e.g., 200 to 400 g-force) centrifugation for a short time (e.g., about 30 minutes). This centrifugation step causes differential movement of the different blood cell types within the tube until all of the cells reach a buoyant equilibrium; at this time, the relatively dense granulocytes and erythrocytes will have moved to the bottom of the tube and formed a solid pellet, the platelets and plasma will have moved to the top portion of the tube, above the density gradient material, and the targeted mononuclear cells will have formed a distinct relatively thin layer, e.g., about 1.5 mm thick, located at the plasma/density gradient interface. Harvesting of the mononuclear cells is then achieved by manually lowering a pipette into the mononuclear cell layer and drawing out a desired volume of cells from this layer. While, in principle, this method is relatively simple to perform, achieving uniformity of results, from one person to the next, as well as from one laboratory to the next, is difficult, at best.

As indicated above, it is recognized that the above process for layering a blood sample atop a density gradient material is a relatively tedious and time-consuming process. A technique that is intended to address these issues is to use a hand-held and hand-operated dispenser that is adapted to inject the density gradient material underneath a blood sample in a tube, rather than to carefully add the blood sample to the top surface of a density gradient layer already in the tube. Such dispenser comprises a narrow dispensing probe that is suitably connected to a hand-held syringe containing the density gradient material. In use, the dispensing probe is manually inserted inside a blood sample-containing tube and advanced through the blood sample to a position proximate the bottom of the tube. The syringe is then activated to slowly inject the density gradient material at the tube bottom, thereby causing the blood sample to rise above it. This so-called "underlaying" technique, and a suitable dispenser construction for carrying it out, are reported in a Technical Report by A. Islam, appearing in Journal of Clinical Pathology, 1995, Vol. 48, pp. 686-688.

While using a density gradient dispenser of the type discussed above theoretically affords certain advantages over the more conventional overlayering technique for disposing a blood sample atop a density gradient material, the use of such a device does not necessarily produce uniform results. Unless the density gradient medium is continually injected at an optimum location at the bottom of the tube, and injected at a relatively steady flow rate, a turbulent disturbance may occur with an unpredictable number of cells from the sample becoming trapped in the density gradient material, and most of those cells will be unavailable for subsequent harvesting. Clearly, there is a need to remove this manual involvement in the cell separation process in order to reduce the variability in the number of cells eventually harvested.

SUMMARY OF THE INVENTION

In view of the foregoing discussion, an object of this invention is to provide a new and improved method for separating and harvesting mononuclear and/or other cells of interest from a whole blood sample, a method that can be readily automated using existing liquid-aspirating and dispensing device.

Another object of this invention is to provide an improved apparatus for separating and harvesting desired cells from a cell sample.

According to a preferred embodiment of the invention, a new and improved method for separating and harvesting cells of interest from a whole blood sample comprises the steps of (a) depositing a predetermined volume of a diluted whole blood sample into a tube; (b) dispensing a predetermined volume of a density gradient solution at a predetermined rate at the bottom of such tube, thereby providing a layer of density gradient solution that underlies the diluted blood sample, such density gradient solution having a density substantially equal to or slightly higher than the density of the cells of interest; (c) centrifuging the tube contents to produce a cell that is predominantly comprised of the cells of interest, such cell layer being located within the tube at a location that overlies the density gradient solution within the tube, (d) advancing the distal end of an aspirating/dispensing probe to a predetermined location within the tube at which an aspiration/dispense port, located at the distal end of the probe, underlies the cell layer by no more than a predetermined distance, and (e) aspirating a predetermined volume of liquid from the tube while the probe remains at such predetermined position, such predetermined volume being sufficient to (i) drop the level of the cell layer to a level in which the probe port becomes immersed in the cell layer, and (ii) enables the probe port to remain within the cell layer until such predetermined volume of liquid has been aspirated, which usually includes a portion of the density gradient solution as well as the cells of interest. Preferably, relative lateral movement is provided between the probe and the tube in order to aspirate cells of interest from different portions of the cell layer.

The invention and its advantages will be better appreciated from the ensuing detailed description of preferred embodiments, reference being made to the accompanying drawings wherein like reference characters denote like parts.

In accordance with another aspect of this invention, apparatus is provided that constructed and programmed to automatically carry out at least steps (b), (d), and (e) of the above-noted process.

BRIEF DESCRIPTION OF THE DRAWINGS

FIGS. 8A and 8B are scattergrams of intracellular cytokine analyses of PBMCs harvested by the automated method of the invention and the manual method of the prior art.

DETAILED DESCRIPTION OF PREFERRED EMBODIMENTS

Figure 1:
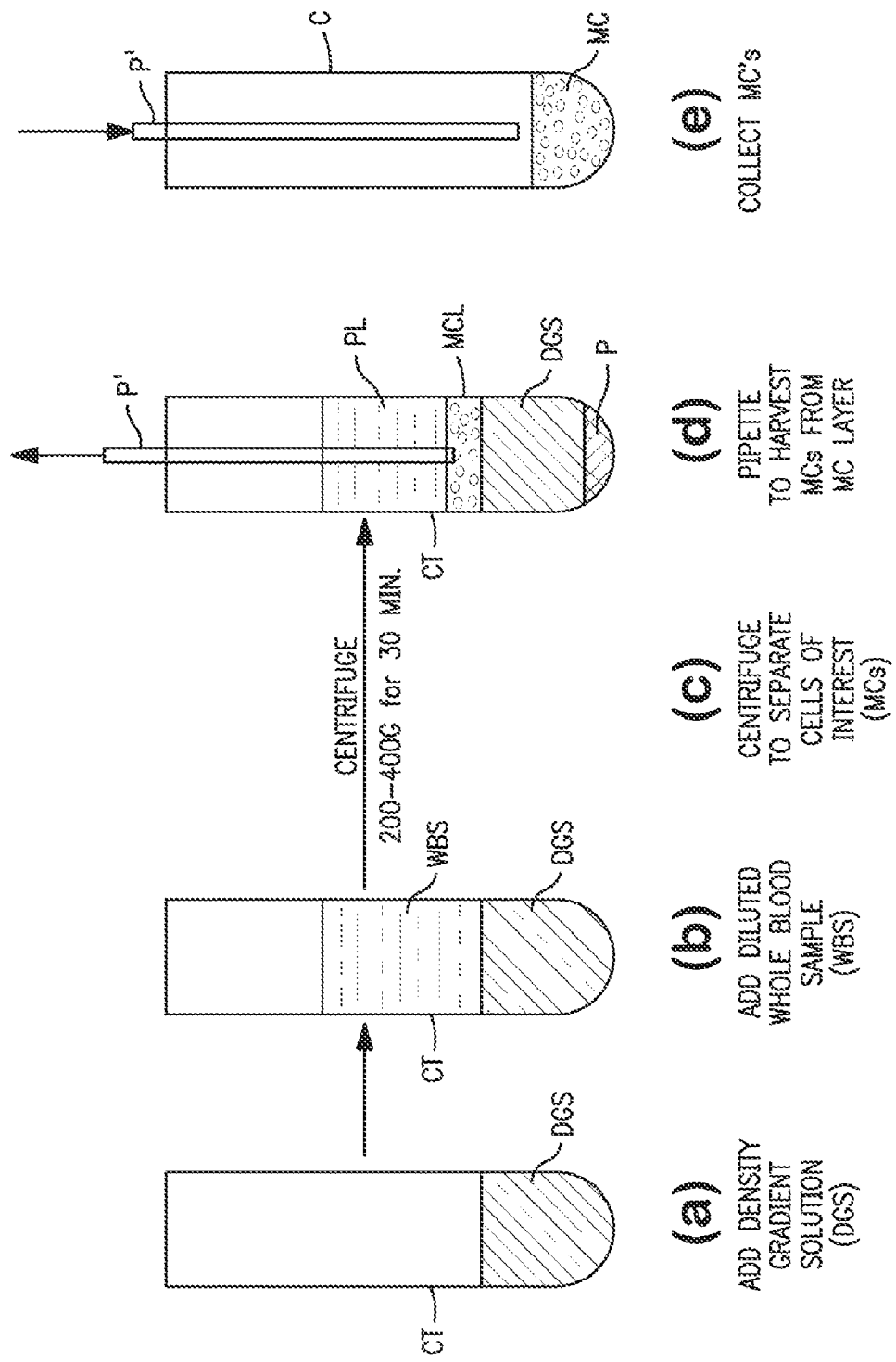
FIG. 1 is a schematic illustration of a prior art method for harvesting mononuclear cells from a whole blood sample.

Referring now to the drawings, FIG. 1 illustrates the conventional, "gold standard" manual method for separating and harvesting cells of interest, e.g., mononuclear cells, MCs, from a peripheral whole blood sample WBS. Cell separation is based on the use of a standard density gradient/centrifugation technique in which diluted blood is carefully layered atop a solution of a suitable density gradient material disposed in a test tube, and then the tube and its contents are subjected to centrifugation. During such centrifugation, differential cell migration, based on the respective buoyant densities of individual cells, results in the formation of several, readily visible, layers of different cell types in the tube. Harvesting of the cell types of interest is then effected by a manually pipetting the cell layer of interest.

Briefly, the method of FIG. 1 normally begins by dispensing a small volume (e.g., 4-5 ml) of a sterile density gradient solution DGS into a suitable centrifugation tube CT, shown as step (a). When mononuclear cells (MCs) are to be harvested from a whole blood sample, the density gradient solution should have a density substantially equal to or slightly higher than the average density of lymphocytes, i.e., 1.077 g/ml. A suitable density gradient solution is that sold under the trademark, Ficoll Paque PLUS, a product of General Electric Healthcare, Uppsala, Sweden. This product is an aqueous solution of Ficoll PM44 and sodium diatrizoate, and it has a density (specific gravity) of precisely 1.077 g/ml. The next step, shown as step (b), is to manually layer a somewhat larger volume (e.g., 7-10 ml) of a diluted whole blood sample WBS atop the density gradient solution. This step requires considerable skill and patience by the laboratory worker for any significant turbulence created at the DGS/WBS interface will usually result in the permanent loss of sample cells into the density gradient solution. As noted above, it has been demonstrated that the layering of a diluted blood sample atop a density gradient solution can also be achieved in the reverse order, i.e., by first introducing the diluted blood sample into the tube, and then using a manually-controlled syringe to inject the density gradient solution beneath the blood sample, thereby causing the blood sample to rise atop the injected solution. While this manual "underlaying" approach may afford certain advantages over the normal "overlayering" approach in terms of speed and convenience, great care must still be taken to assure that (i) the dispenser tip enters and exits the whole blood sample without introducing any turbulence, (ii) the dispensing tip of the syringe is always maintained at the bottom of the tube during the dispensing process, and (iii) the dispensing rate, which is manually controlled, is slow and continuous so that no bubbling or significant turbulence is produced by the introduction of the density gradient solution at the tube bottom. Due to these considerations, the "overlaying" method is usually the method of choice for creating a sample layer atop the density gradient material.

Having manually layered a diluted whole blood sample atop a suitable density gradient solution, the next step, indicated as step (c), is to place the tube in a centrifuge where the contents are spun at a relatively slow rate (e.g., to achieve a 200-400 g-force) for a short time, (e.g., 15-30 minutes). During this centrifugation step, the relatively dense red blood cells, as well as the granulocytes of the white cell population, settle through the density gradient solution and form a pellet P at the bottom of the tube. Meanwhile, the mononuclear cells MCs, composed of lymphocytes (having a density of 1.077 g/ml) and monocytes (having a density of 1.065 g/ml), form a readily thin (e.g., 1.5 mm thick) mononuclear cell layer MCL, which is translucent and readily visible atop the density gradient layer. The remainder of the tube contents (above the mononuclear cell layer) comprises a blood plasma layer which contains platelets having a significantly lower density than the mononuclear cells.

Harvesting of the now-separated mononuclear cells from the cell layer MCL is commonly achieved using a hand-held Pasteur pipette P'. During such harvesting of cells, shown as step (d), the pipette tip is manually advanced through the plasma layer and carefully inserted into the MC layer. During the pipetting process, care must be taken that the pipette tip remains submerged in the MC layer; otherwise, substantial volumes of the underlying density gradient solution, or the overlying plasma, will be aspirated. After each of multiple pipetting steps to assure that most of the cells in the MC layer have been harvested, the aspirated mononuclear cells are collected (step (e)) in a container C, e.g., another centrifugation tube where the cells are prepared for subsequent analysis. This process usually includes the steps of mixing the cells with a phosphate buffer solution (PBS), centrifuging the buffered solution to produce a pellet of mononuclear cells, decanting the supernatant, breaking up the pellet, re-suspending the mononuclear cells in a buffer, and finally analyzing the mononuclear cell solution.

As will be appreciated from the above description, the "gold standard" method of harvesting cells of interesting from a whole blood sample is fraught with opportunities for errors to occur. Even the slightest involuntary movement by one who initially layers the blood sample prior to centrifugation, be it by the "underlaying" or "overlaying" approaches, or by one who manipulates the pipette for cell harvesting can produce results that must be discarded. A better, more consistent, reliable and faster approach is needed.

Figure 2:
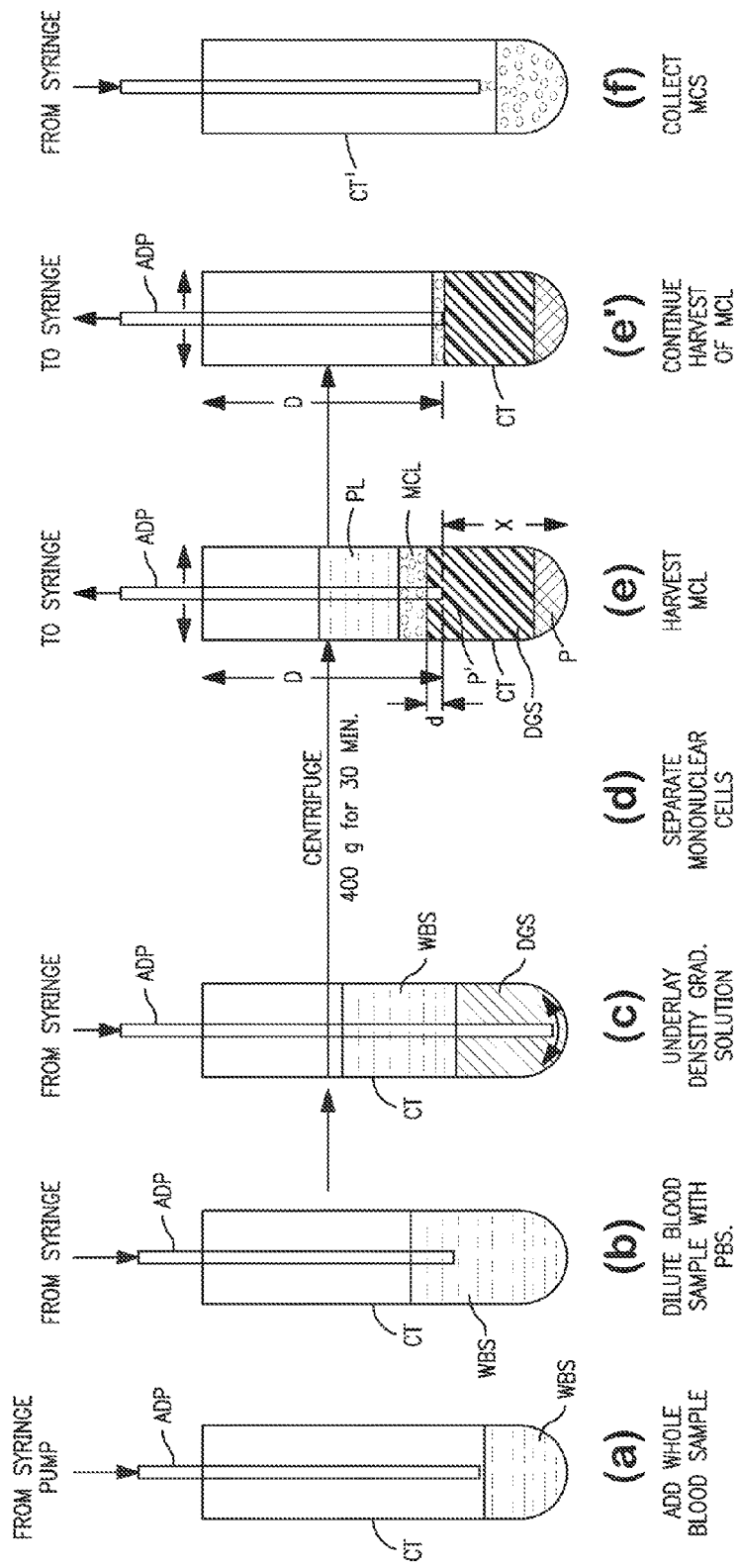
FIGS. 2 and 3 are schematic illustrations of preferred methods of the invention.

Referring now to FIG. 2, the method of separating and harvest cells in accordance with the present invention is one that enables the most troublesome steps of the prior art's manual method (described above) to be readily automated. While this method may be carried out manually, it is highly preferred that all but the centrifugation step, which is carried out by another automated instrument off-line, be carried out by a single automated instrument, for example, a modified version of the Coulter PrepPlus™ Sample Preparer, made by Beckman Coulter, Inc, Fullerton, Calif. Standard features of the PrepPlus instrument that render it especially useful in carrying out a preferred embodiment of the invention include: (1) a cap-piercing aspirating/dispensing probe, a Teflon®-coated, stainless steel pipette that is capable of reaching the bottom of a standard 15 ml centrifugation tube; (2) an X/Y/Z probe-drive for precisely advancing the probe (via three precision stepper motors) in three mutually-perpendicular planes in order to precisely position the distal end of the probe within any one of a plurality of different tubes and containers located at various locations atop the work surface of the instrument; (3) a stepper-motor-controlled syringe pump for aspirating precise volumes of liquid from a container through the probe, and for dispensing such volumes through the same probe at precisely controlled rates, and (4) a programmable controller by which the probe movement and liquid aspirate and dispense rates and volumes can be precisely controlled as needed in carrying out the method of the invention. In addition to the need for suitably programming the movement of the aspirating/dispensing probe and its liquid dispense rate in order to carry out the method steps described below, the PrepPlus instrument is preferably modified (i) to include a 10 ml syringe pump, in place of the 1.0 ml syringe pump provided with the instrument, and, (ii) in order to prepare multiple samples for centrifugation without the need for physically handling each individual tube, to replace the tube carousel presently used in such instrument to support multiple tubes during sample preparation, with a standard centrifugation "tube adapter" of the type commonly used to support multiple tubes during centrifugation within a centrifuge instrument. An instrument for carrying out the method of the invention is schematically shown in FIGS. 4A and 4B.

Figure 4A:
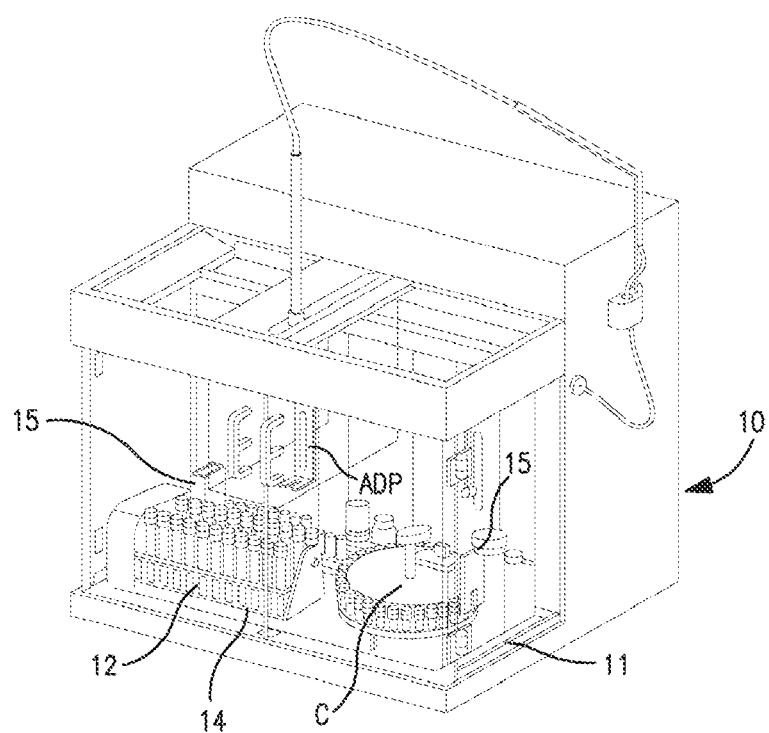
FIGS. 4A and 4B are perspective views of preferred apparatus for carrying out the methods of invention.
Figure 4B:
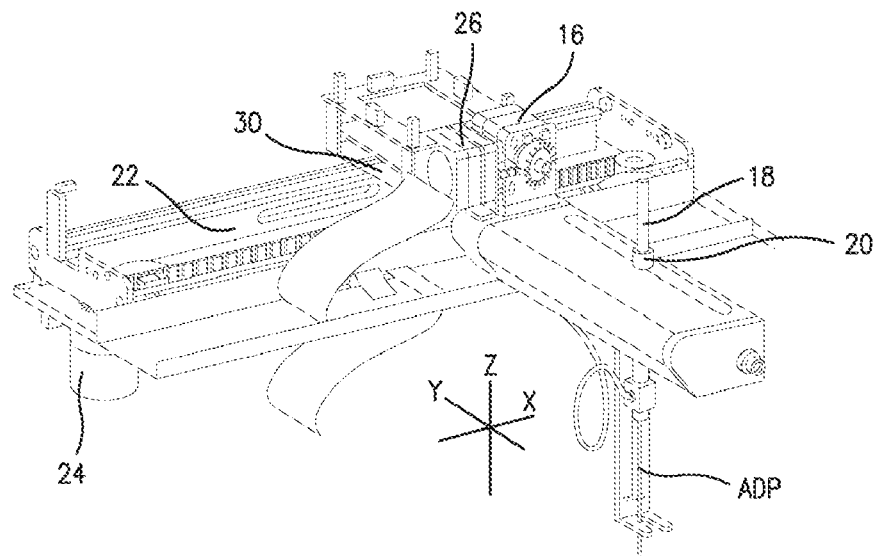

Referring briefly to FIG. 4A, the apparatus of the invention is shown as comprising a modified version of the PrepPlus instrument noted above. Such instrument comprises a housing 10 having a work platform 11 that supports a tube rack 12 adapted to hold a plurality of sealed specimen or sample containers 14 in an upright position. The work platform also supports a tube carousel for supporting a plurality of tubes 15 in which sample preparation can occur, and a variety of reagent containers that hold the various reagents with which the sample specimens are to be mixed. An aspirating/dispense probe ADP (better shown in FIG. 4B) is movably mounted within the housing in the space above the specimen containers. As shown in FIG. 4B, the probe is mounted for movement along three mutually perpendicular axes, X, Y and Z, and, hence, the distal end of the probe, through which liquid aspiration and dispensing occurs, can access the contents of any tube or container in the housing. The proximal end of the probe is fluidly connected to a bi-directional pump, i.e., a syringe pump, having a movable actuator that controls the mode of the pump, i.e., aspirating or dispensing, and the rate of liquid aspiration and dispensing. Movement of the pump actuator is controlled by a precision stepper motor that operates under the control of a programmable controller comprising a microprocessor. Probe movement along the Z axis, so as to enable the probe tip to enter and exit from different containers, is controlled by a Z stepper motor 16 that serves to selectively advance a vertically-oriented linear rack 18 in opposite directions in a bearing 20. The Z-movement mechanism is slidably mounted on a linear frame 22 extending along the X axis, and its movement along the X axis is controlled, via a belt drive system, by the X stepper motor 24. Movement along the probe assembly along the Y axis is controlled by the Y stepper motor 26 which advances the probe-support assembly along a frame 30 extending along the Y axis. The operation of all stepper motors is controlled by the programmable system controller. A probe washer 15 is provided on the work platform to was the probe, inside and out, after each cycle of use.

As noted above, the PrepPlus instrument has been modified to carry out the method of the invention. In particular, the 1.0 ml (maximum capacity) syringe pump that is normally used in this instrument to aspirate relatively minute sample and reagent volumes, of the order of microliters, has been replaced with a 10 ml pump. Further, the microprocessor that controls probe movement and its aspirate/dispense rates must be suitably reprogrammed to achieve, e.g., the desired lateral movement to harvest cells from all portions of the separated cell layer, and to dispense and aspirate liquid, at the desired rates and from the appropriate levels within the tube, etc. in order to carry out the underlaying of density gradient material and the harvesting of cells of interest from the separated cell layer resulting from centrifugation. Preferably, the tube carousel C is replaced with the above-mentioned tube adapter which is adapted to hold a plurality of centrifugation tubes within a conventional centrifugation instrument during the centrifugation process. Such tube adapter is releasably supported on the work platform 12 and, after each tube in the adaptor has been prepared for centrifugation, the tube adaptor is removed from the instrument and manually transported to the centrifuge where all of the tubes in the adaptor are centrifuged simultaneously. As noted, This modification avoids the necessity of having to manually transfer each tube from the carousel to the centrifugation bucket prior to centrifugation.

Referring again to FIG. 2, the preferred method of the invention is shown and described, as in the case of the method of FIG. 1, as being used to separate and harvest mononuclear cells MC from a whole blood sample. The liquid aspirating and dispensing steps of the method are illustrated as being carried out by the aspirating and dispensing probe ADP and the programmable syringe pump of the PrepPlus instrument. The method of the invention begins by dispensing a predetermined volume (e.g., 4.0 ml) of a EDTA-treated or Heparinized whole blood sample into a centrifugation tube CT (e.g., a standard 15 ml tube). This step may be carried out by programming the probe to enter a selected one of a plurality of sealed vials V supported by a rack R, aspirating the desired sample volume, then moving to a selected tube in the centrifugation bucket and dispensing the just aspirated volume of sample. Having dispensed a volume of whole blood sample into a particular tube CT, a like volume of PBS (4.0 ml) is added to provide a diluted, 1:1, whole blood sample within tube CT. The addition of the PBS to the blood sample is effected by programming the PrepPlus instrument to aspirate a desired volume of PBS from an on-board supply container and to dispense such volume into the sample-containing tube through probe ADP. The PBS is dispensed at a controlled rate adapted to achieve thorough mixing of the liquids.

The next step, shown as step (c), is to carefully underlay the diluted whole blood sample in tube CT with a predetermined volume (e.g., 4.0 ml) of density gradient material, in this case, the above-noted Ficoll Paque PLUS solution. This step may be carried out by programming the PrepPlus instrument to aspirate such predetermined volume of the density gradient material from an on-board supply container, and to dispense such volume in close proximity to the tube bottom at a slow and controlled rate so as not to disturb the overlying blood sample. As indicated above, movement of the probe is precisely controlled in the PrepPlus instrument by precision stepper motors, and the liquid-dispensing velocity and acceleration profiles are precisely controlled by a precision stepper motor that operates under the control of an on-board microprocessor to control the actuator movement of the bi-directional syringe pump through which the density gradient solution is delivered. As the density gradient solution is added to the tube bottom, the diluted whole blood sample rises above it, as described above. Thereafter, the probe is extracted from the tube at a steady rate, again so as to avoid the creation of any turbulence within the tube.

Upon creating a layer of whole blood atop the density gradient solution in a centrifugation tube, the tube is manually removed from the sample-preparing apparatus and centrifuged, as described above, to physically separate the cells of different types within the tube, the cell layer of interest (i.e., mononuclear cells) appearing at a location immediately above the density gradient material. As indicated above, this centrifugation tube may be one of a many such tubes supported by the tube adaptor, and after each tube has received a blood sample with an underlayer of density gradient material in the manner described, the adaptor may manually removed from the aspirating/dispensing instrument, and placed in a centrifuge where all tubes are processed together to achieve cell separation.

Now, in accordance with an important aspect of the invention, the cells of interest (i.e., the mononuclear cells) are harvested from the cell layer (MCL) by advancing the distal end of an aspirating/dispensing probe (e.g., probe ADP of the PrepPlus instrument) to a predetermined location within the tube at which an aspiration/dispense port P', located at the extreme tip of distal end of the probe, underlies the cell layer by no more than a predetermined distance d, shown in FIG. 2 as step (e). Then, a predetermined volume of liquid is aspirated from the tube while the probe remains at such predetermined location. During this aspiration, the level of the mononuclear cell layer will continually drop in the tube until the cell layer fully immerses the aspiration port of the probe, after which the cell layer will gradually diminish in thickness, as shown in step (e'), as the mononuclear cells are aspirated from it. The predetermined volume to be aspirated is that which is sufficient to (i) drop the level of the MC cell layer to a level at which the probe port becomes immersed in the cell layer, and (ii) enable the harvesting of at least 90% of the mononuclear cells in the cell layer. The ideal volume aspirated depends on the diameter of the tube and the initial volume of the blood sample. For a standard 15 ml centrifugation tube, the ideal volume to be aspirated is about 3.0 ml. Preferably, during harvesting of the mononuclear cells from the cell layer, relative lateral movement (in the X/Y plane) is produced between the probe tip and the tube, shown by the laterally extending arrows in step (e), so that cells at different lateral locations within the cell layer are aspirated. In a programmable instrument of the type described above, the probe may be programmed, for example, to scribe a "figure eight" or a spiral pattern, beginning at the center of the tube where most of the cells are located, during the harvesting of cells.

In an automated process, cell harvesting is achieved by advancing the aspirating/dispense probe tip into the tube by a predetermined distance D, which corresponds to the minimum level at which the bottom of the MC layer is expected to appear in the tube. This minimum level, indicated by the distance X (shown in step (e) of FIG. 2), is measured from the bottom of the tube. Such level can be determined either by calculation or by empirical measurements made on a multitude of samples. Since the diameter of the tube is a constant, as are the parameters of the centrifugation step and the respective volumes of the blood sample and density gradient material added to the tube, the MC layer will always appear at the same minimum distance from the bottom of the tube, plus a small deviation (corresponding to distance d). This deviation may be caused by slight variations in tube size (due to manufacturing tolerances) and certain characteristics of the blood sample that affect, for example, the density of the pellet P of red cells and granulocytes formed at the bottom of the tube after centrifugation. In a standard 15 ml centrifugation tube, which has a diameter of 15 mm, distance d corresponds to a volume of 0.3 ml. Thus, in harvesting the cells from the MC cell layer, the aspirating/dispensing probe is advanced by a distance D into the tube, and 3.0 ml of liquid is aspirated. In the case, as shown in the drawing, where the bottom of the MC layer is at its maximum deviation from its minimum level, i.e., a distance X+d from the bottom of the tube, the first 0.3 ml of the aspirated liquid will comprise primarily density gradient solution and a relatively small number mononuclear cells; note, however, that the rate at which such cells are harvested will continually increase as the MC cell layer moves (drops) toward the aspirating port of the probe during aspiration. After 0.3 ml of liquid has been aspirated, the probe's aspiration port will now be fully immersed in the cell layer, and only mononuclear cells will be aspirated for the succeeding 2.7 ml of liquid aspiration. In the case where the bottom of the MC layer is initially located at the minimum level, i.e., a distance X from the bottom of the tube, the tip of the probe will coincide with the bottom of the MC layer, and mononuclear cells will be harvested from the cell layer during the entire 3.0 ml of aspiration.

After aspirating a predetermined volume of liquid from the tube, most of which contains the mononuclear cells of interest, the probe is slowly removed from the tube and the aspirated liquid is dispensed into an centrifugation tube CT', e.g., a 50 ml centrifugation tube. The harvested cells are then diluted with PBS, centrifuged to form a pellet, washed to rid the cells of any residual gradient density material, resuspended in PBS and analyzed for viability.

From the foregoing, it will be apparent that method of the invention readily lends itself to automation using a programmable liquid aspirating and dispensing apparatus of the type employed in the PrepPlus Sample Preparing Instrument. Though not intended for the purpose of preparing samples for cell-separation and harvesting, the PrepPlus instrument, when suitably programmed and modified as described above, is ideally suited to carry out the method of the invention due to its ability to precisely translate a liquid-aspirating and dispensing probe in three (X/Y/X) dimensions, to precisely position the probe at the desired depths in the container in which the method is carried out, and to aspirate and dispense liquids at carefully controlled rates so as to avoid any substantial turbulence at the probe tip. The fact that the method of the invention, when automated, can achieve results that are equal or better that the results attained by the conventional manual method for harvesting cells is evident from the following graphs, bar charts, histograms, and scattergrams.

Figure 5:
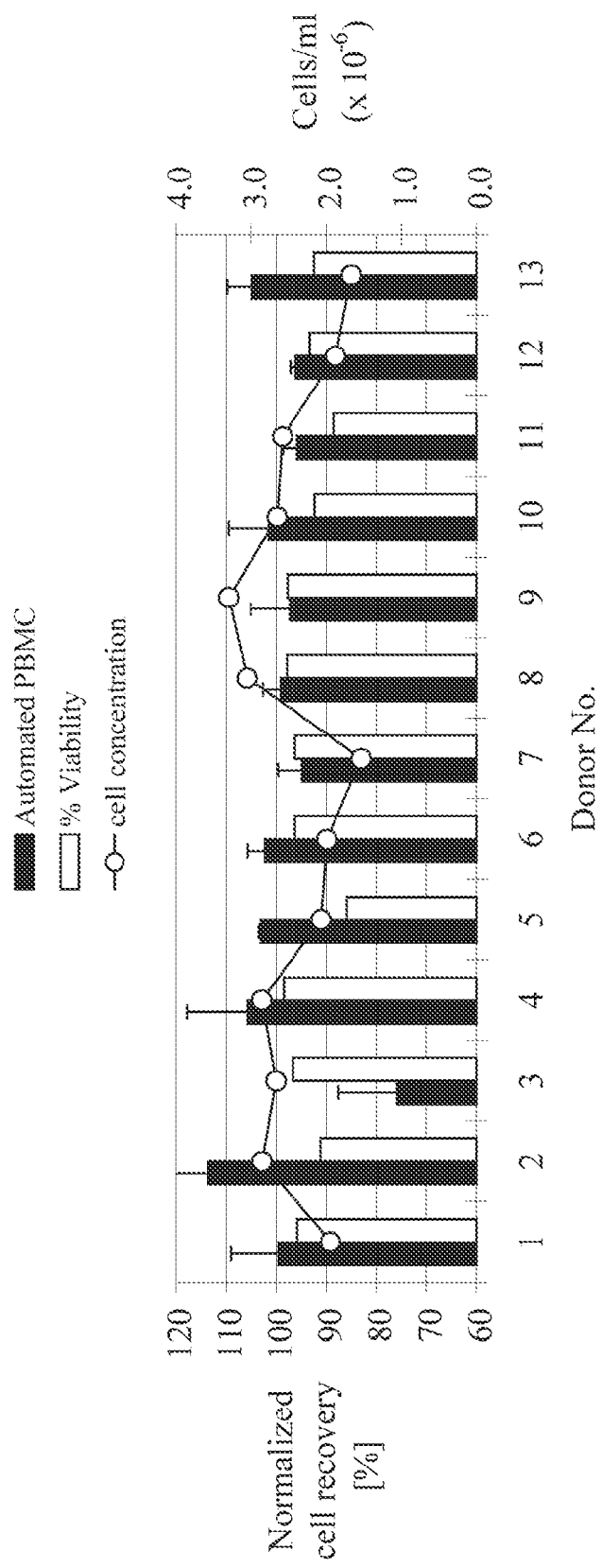
FIG. 5 is a chart comparing cell recoveries and viabilities for cells separated and harvested by the manual method of the prior art and the automated method of the invention.

The combined bar chart and graph of FIG. 5 compares the percentage of cells recovered (i.e., harvested) from peripheral whole blood samples provided by 13 different donors using both the manual cell separating and harvesting method, described with reference to FIG. 1, and by the method of the invention, as automated using the above noted PrepPlus instrument. Cell recovery results for the automated method were normalized to the manual results for the corresponding sample. Each result is shown as the average (based on duplicates or triplicates per donor)±standard deviation. Viability results for the automated method are shown as the average of three replicates for each donor. All viability results were obtained using the Vi-Cell™ XR Cell Viability Analyzer (Beckman Coulter, Inc.). Cell viability results for the manual method were comparable ($\Delta \leq 3\%$) to those from the automated method (data not shown). Cell concentration results are the average of three replicates per automated sample determined using the Vi-Cell XR analyzer. Measurements are based on 100 microliter-aliquots from cells diluted in 2-2.5 ml of PBS or MEM/10% FCS. The Vi-Cell protocol conditions for all these results is described in the product literature.

Figures 6A, 6B:
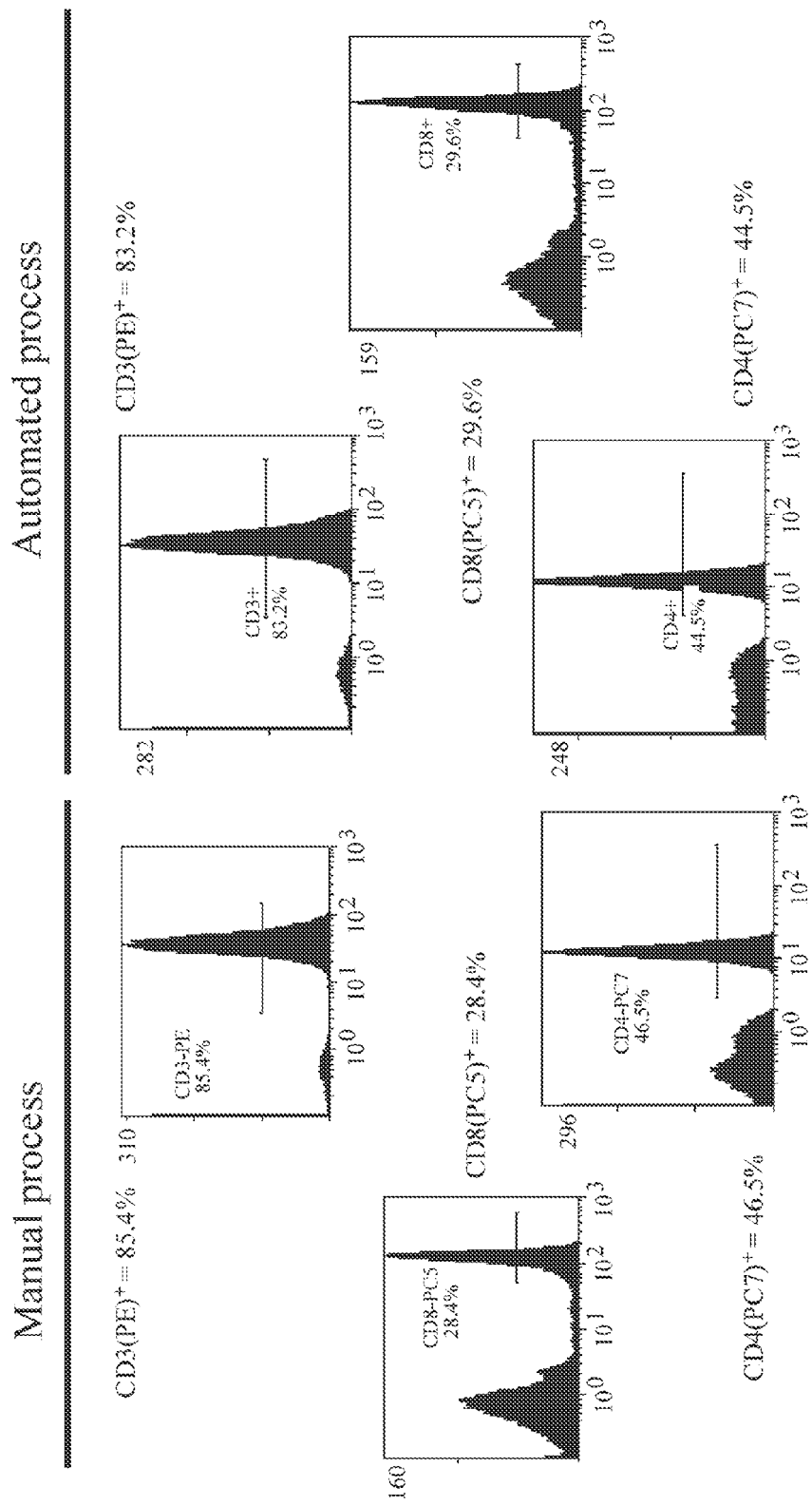
FIGS. 6A and 6B are histograms comparing the phenotypic characterizations of cells harvested manually versus cell harvested by the method of the invention.

In the histograms of FIGS. 6A and 6B, a phenotypic comparison of cells harvested by the manual method of the prior art and by the automated method of the invention is shown. These results illustrated are for representative markers for one donor subjected to phenotypic characterization. PBMCs (peripheral blood mononuclear cells) obtained by manual and automated methods, from same donor, were stained in two tubes containing various monoclonal antibodies, each being conjugated with a fluorochrome. Tube #1 contained 50 µl of cells ($2-3 \times 10^6$ cells/ml) and 10 or 20 µl of CD 14-FITC, CD19-PE, CD3-ECD, CD56-PC5, and CD45-PC7, 2); Tube #2 contained 50 µl of cells ($2-3 \times 106$ cells/ml) and 10 or 20 µl of CD19-FITC, CD3-PE, CD45-ECD, CD8-PC5, and CD4-PC7. The tubes were incubated at RT for 15 minutes, and 4 ml of PBS were added. The tubes were then centrifuged at 300 g for 5 minutes, and the resulting cell pellet was re-suspended in 0.5 ml of PBS. All samples were analyzed on the Cytomics FC500™ Flow Cytometer (Beckman Coulter) based on a protocol to pre-gate on lymphocytes and CD45$^+$ cells for a total of 300 seconds. As is readily apparent from the histograms of FIGS. 6A and 6B, the two methods for harvesting cells appear to correlate well in terms of their respective phenotypic characterizations.

Figure 7:
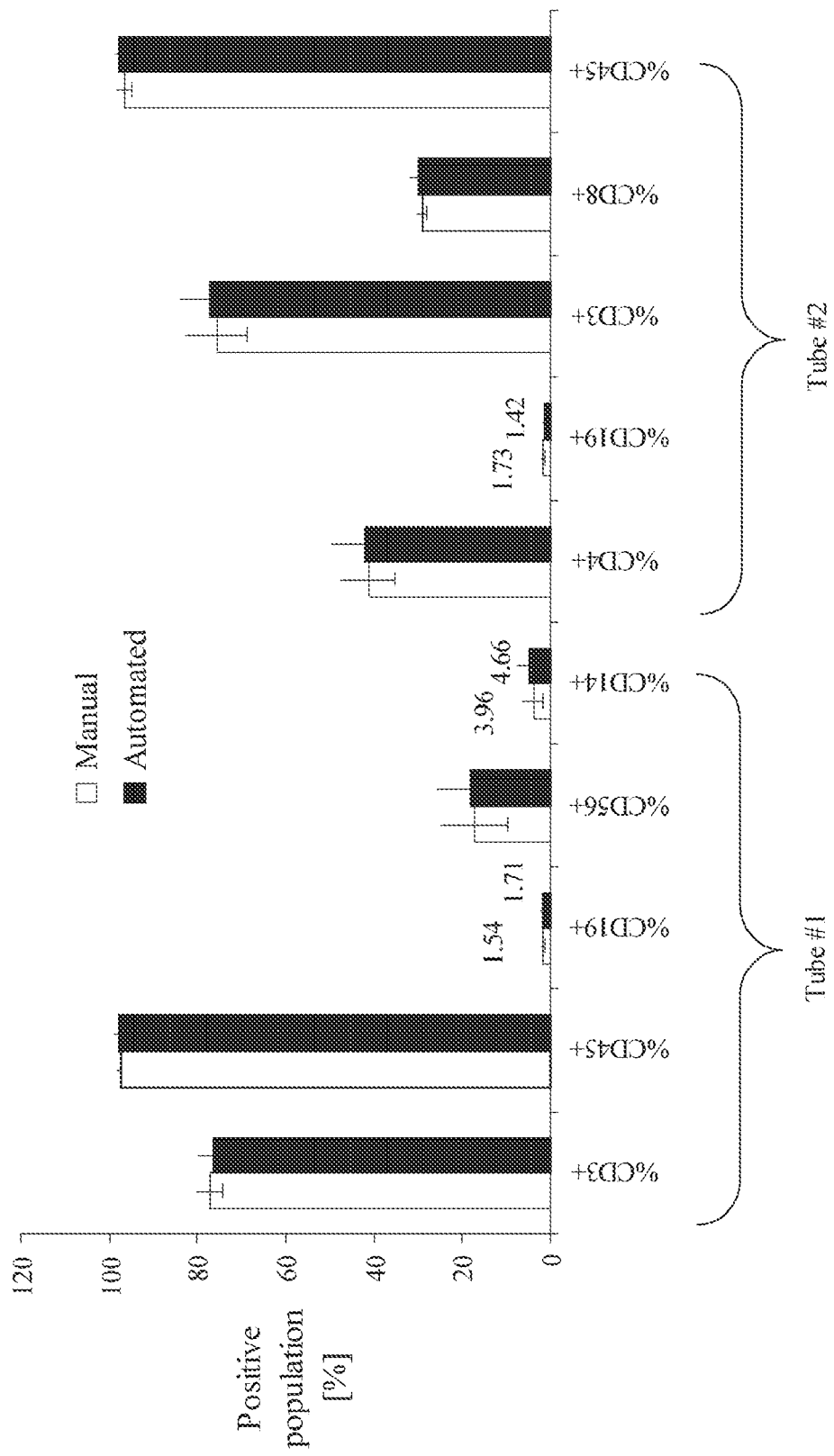
FIG. 7 is a bar chart comparing the percentages of cells harvested by the automated method of the invention and by the prior art that had a positive response to seven different antibodies.

The bar graph of FIG. 7 compares the percent of mononuclear cells that have tested positive to each of seven different antibody/fluorescent dye conjugates. For each conjugate, the dark bars represent the percentage of cells harvested by the automated method of the invention, and the clear bars represent cells harvested by the manual method. This data is based on four representative donors subjected for phenotypic profiling. Each data point represents the average±standard deviation based on duplicates or triplicates for each test condition per donor. All samples were stained and analyzed on the Cytomics FC500 (methods for sample preparation and analysis is detailed elsewhere). As indicated, the results are strikingly similar, indicating that the method of the invention has little or no adverse effect on the harvesting of cells vis-à-vis the manual method.

The scattergrams of FIGS. 8A and 8B respectively illustrate an intracellular cytokine analysis of PBMCs that have been isolated by the automated method of the invention, and by the manual method of the prior art. The results are representative of one experiment where automated and manually isolated PBMCs, from the same donor, were subjected to identical stimulation and sample preparation and analysis. Stimulation. Freshly isolated PBMCs were rested overnight at $5-10 \times 10^6$ cells/ml in RPMI 1640/10% FCS/pen/strep, 37° C., and 5% $CO_2$. Cells were then stimulated with staphylococcal enterotoxin-B (SEB) and anti-CD28 at final concentrations of 2 and 3 µg/ml, respectively. After 2 hours, Brefaldin A was added at a final concentration of 5 µg/ml, and the cells were incubated for 16 hours at 37° C. in 5% CO2. Cell surface and intracellular staining was performed using a modified and automated method using IntraPrep™ Permeabilization Reagent (Beckman Coulter, Inc.). Cell surface and intracellular staining reagents included IFNg-FITC, IL2-PE, CD8-ECD, CD3-PC5, CD4-PC7. All samples were then analyzed in a Cytomics FC500 cytometer using a predefined protocol with initial gating on lymphocytes and CD3$^+$ cells and a total analysis time of 300 seconds.

From the above examples, it is apparent that the automated method of the invention provides cells that are comparable to the cells harvested manually in terms of number, viability phenotypic profile, and cell function characterization. The data shows that the automated method of the invention can routinely recover more than 93% of the number of cells achieved by the best manual method.

In the description above, it is noted that it is desirable to produce lateral movement (i.e., in the X/Y plane) during the aspiration of the cell layer in order to harvest cells from different locations in the layer. An alternative approach is to make multiple aspirations, each time shifting the point of entry of the aspiration probe into the cell layer. For example, the first and second aspirations may be made at the geometric center of the tube (in the X/Y plane), which is where most of the cells of interest congregate after centrifugation. Then, four more aspirations can be made in each of the surrounding four quadrants. In this embodiment, the total volume aspirated by the six aspirations will equal the single aspiration made during the cell harvesting step described above.

Figure 3:
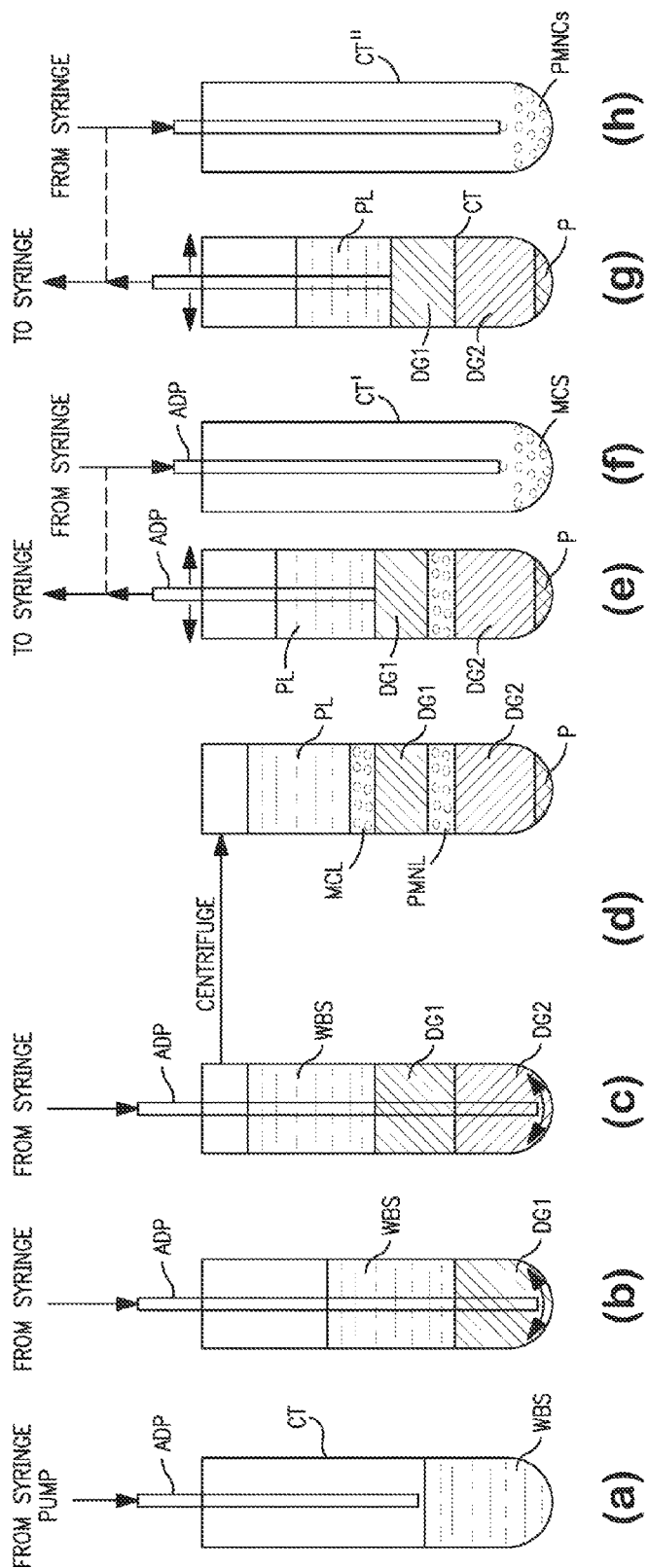

While the invention has been described with reference to the harvesting of mononuclear cells, it will be apparent that other cell types may be separated and harvested by properly selecting the gradient material. Further, other cell types may be separated and harvested within the same tube of whole blood utilizing a discontinuous density gradient method. For example, referring to FIG. 3, a diluted whole blood sample in tube T may be underlaid with two different density gradient materials, DG1 and DG2. DG1 may be formulated to isolate mononuclear cells (MCs), while DG2 may be formulated to isolate polymorphonuclear cells (PMNCs), which have a greater density of 1.12 g/ml. As in the method described with reference to FIG. 2, the aspirating/dispensing probe used to underlay the blood sample with the density gradient material (s) is found in an automated sample preparer, e.g., the Prep-Plus instrument discussed above. The probe is programmed to sequentially dispense, each time at the bottom of the tube, first the density gradient material having the lower density (DG1), and then the higher density material, DG2. Upon underlaying the blood sample with the two density gradient materials, the tube contents are subjected to centrifugation, which operates to separate the cells of interest into two distinctive cell layers, with the MC layer being formed atop DG1 and the PMNC layer being formed atop DG2. The tube is then returned to the sample-preparing instrument where the aspiration probe is programmed to (a) first advance to a level slightly below (by a distance d) the nominal position of the MC layer and to aspirate and dispense cells in the manner described above until a desired volume from the MC layer is attained, and then, after washing of the probe, to (b) advance to a level slightly below (again by distance d) the nominal position of the PMNC layer and to aspirate and dispense cells in the manner described above.

The invention has been described with reference to preferred embodiments. It will be understood, however, that various modification and changes can be made without departing from the spirit of the invention, and such variations are intended to fall within the scope of the appended claims.

What is claimed is:

1. A method for separating and harvesting cells of interest from a whole blood sample, said method comprising the steps of:

(a) depositing a predetermined volume of a diluted whole blood sample into a tube, wherein said diluted whole blood sample comprises said cells of interest, said cells of interest having a cell density; and wherein said tube comprises a bottom and a diameter;

(b) dispensing a predetermined volume of a density gradient solution at a predetermined rate at said bottom of said tube, thereby providing a layer of said density gradient solution that underlies said diluted whole blood sample, said density gradient solution having a density substantially equal to or slightly higher than said cell density of said cells of interest;

(c) centrifuging contents of said tube to produce a cell layer comprising said cells of interest, said cell layer overlying said density gradient solution;

(d) advancing a distal end of an aspirating/dispensing probe to a predetermined location within said tube at which probe port, located at said distal end of said aspiration/dispense probe, underlies said cell layer by no more than a predetermined distance, wherein said predetermined distance is based upon a measurement from said bottom of said tube and said cell layer, said predetermined volume of said diluted whole blood sample, said predetermined volume of said density gradient solution, and said diameter of said tube; and (e) aspirating a predetermined volume of liquid from said tube using a predetermined relative lateral movement between said aspiration/dispense probe and said tube in order to aspirate said cells of interest from different portions of said cell layer, said predetermined volume being sufficient to (i) drop said cell layer to a level in which said probe port becomes immersed in said cell layer, and (ii) enable said probe port to remain in said cell layer until such said predetermined volume of liquid has been aspirated.

2. The method as defined by claim 1 wherein said dispensing step is achieved by advancing said distal end of said aspirating/dispensing probe through said diluted whole blood sample to a vicinity of said bottom of said tube; and dispensing said predetermined volume of said density gradient solution at said bottom of said tube.

3. The method as defined by claim 2 wherein said aspiration/dispense probe is advanced a predetermined distance into said tube to dispense said density gradient solution in the vicinity of the tube bottom.

4. The method as defined by claim 2 wherein said density gradient solution is dispensed at a predetermined rate sufficient to minimize turbulence in said diluted whole blood sample.

5. The method as defined by claim 1 wherein said predetermined relative lateral movement is provided by moving said aspiration/dispense probe relative to said tube.

6. A method for separating and harvesting cells of interest from a whole blood sample, said method comprising the steps of:

(a) depositing a predetermined volume of a diluted whole blood sample into a tube, wherein said diluted whole blood sample comprises said cells of interest, said cells of interest having a cell density; and wherein said tube comprises a bottom and a diameter;

(b) advancing a tip of an aspirating/dispensing probe through said diluted whole blood sample to a vicinity of said bottom of said tube;

(c) dispensing a predetermined volume of a density gradient solution at said bottom of said tube through said tip of said aspirating/dispensing probe, thereby providing a layer of said density gradient solution that underlies said diluted whole blood sample, said density gradient solution having a density substantially equal to or slightly less than said cell density of said cells of interest;

(d) centrifuging contents of said tube to produce a cell layer comprising said cells of interest, said cell layer overlying said density gradient solution;

(e) advancing said tip of said aspirating/dispensing probe to a predetermined distance into said tube to a position in which said tip has passed through said cell layer and has entered said density gradient solution, wherein the predetermined distance is based upon a measurement from said bottom of said tube and said cell layer, said predetermined volume of said diluted whole blood sample, said predetermined volume of said density gradient solution, and said diameter of said tube;

(f) aspirating a first predetermined volume of said density gradient solution from said tube using a first predetermined relative lateral movement between said aspirating/dispensing probe and said tube in order to aspirate said cells of interest from different portions of said cell, said first predetermined volume being sufficient to drop said cell layer to a level at which said tip of said aspirating/dispensing probe is immersed in said cell layer at termination of said aspiration;

(g) removing said aspirating/dispensing probe from said tube and dispensing said first predetermined volume of said density gradient solution into a container;

(h) again advancing said tip of act said aspirating/dispensing probe into said tube by said predetermined distance to position said tip within said cell layer;

(i) aspirating a second predetermined volume of said density gradient solution from said tube using a second predetermined relative lateral movement between said aspirating/dispensing probe and said tube in order to aspirate said cells of interest from different portions of said cell layer, said second predetermined volume being sufficient to (i) drop said cell layer to a level in which said probe port becomes immersed in said cell layer, and (ii) enable said probe port to remain in said cell layer until said second predetermined volume of liquid has been aspirated;

(j) removing said aspirating/dispensing probe from said tube and dispensing said second predetermined volume of liquid into said container; and (k) repeating steps (h), (i) and (j) to provide a desired predetermined volume of said cell layer comprising said cells of interest in said container.

7. A method for separating and harvesting a first and a second cells of interest from a whole blood sample, said method comprising the steps of:

(a) depositing a predetermined volume of said whole blood sample into a tube, wherein said whole blood sample comprises said first cells of interest and said second cells of interest; wherein said first cells of interest and said second cells of interest are of a different type of cell; wherein said first cells of interest have a first cell density and said second cells of interest have a second cell density; wherein said second cell density of said second cells of interest is greater than said first cell density of said first cells of interest; and wherein said tube comprises a bottom and a diameter;

(b) dispensing a predetermined volume of a first density gradient solution at a predetermined rate at said bottom of said tube, thereby providing a layer of said first density gradient solution that underlies said whole blood sample, said first density gradient solution having a density substantially equal to or slightly higher than said first cell density of said first cells of interest;

(c) dispensing a predetermined volume of a second density gradient solution at a predetermined rate at said bottom of said tube, thereby providing a layer of said second density gradient solution that underlies said layer of said first density gradient solution, said second density gradient solution having a density substantially equal to or slightly higher than said second cell density of said second cells of interest;

(d) centrifuging contents of said tube to produce a first cell layer and a second cell layer, said first cell layer and said second cell layer being spaced apart in said tube by said layer of said first density gradient solution, wherein said first cell layer predominantly comprises said first cells of interest, said first cell layer overlying said first density gradient solution;

(e) advancing a distal end of an aspirating/dispensing probe to a first predetermined location within said tube at which probe port, located at said distal end of said aspiration/dispense probe, underlies said first cell layer by no more than a first predetermined distance, wherein said first predetermined distance is based upon a measurement from said bottom of said tube and said first cell layer, said predetermined volume of said whole blood sample, said predetermined volume of said first density gradient solution, said predetermined volume of said second density gradient solution, and said diameter of said tube;

(f) aspirating a first predetermined volume of liquid from said tube using a first predetermined relative lateral movement between said aspiration/dispense probe and said tube in order to aspirate said first cells of interest from different portions of said first cell layer, said first predetermined volume being sufficient to (i) drop said first cell layer to a level in which said probe port becomes immersed in said first cell layer, and (ii) enable said probe port to remain in said first cell layer until said first predetermined volume of liquid has been aspirated;

(g) advancing said distal end of said aspirating/dispensing probe to a second predetermined location within said tube at which said probe port, underlies said second cell layer by no more than a second predetermined distance, wherein said second predetermined distance is based upon a measurement from said bottom of said tube and said second cell layer, said predetermined volume of said whole blood sample, said predetermined volume of said first density gradient solution, said predetermined volume of said second density gradient solution, and said diameter of said tube; and (h) aspirating a second predetermined volume of liquid from said tube using a second predetermined relative lateral movement between said aspiration/dispense probe and said tube in order to aspirate said second cells of interest from different portions of said second cell layer, said second predetermined volume being sufficient to (i) drop said second cell layer to a level in which said probe port becomes immersed in said second cell layer, and (ii) enable said probe port to remain in said second cell layer until said second predetermined volume of liquid has been aspirated.

* * * * *